(12) United States Patent
Kim et al.

(10) Patent No.: US 11,572,401 B2
(45) Date of Patent: Feb. 7, 2023

(54) GENETICALLY ENCODED CALCIUM INDICATORS AND METHODS OF USE

(71) Applicant: Howard Hughes Medical Institute, Chevy Chase, MD (US)

(72) Inventors: Douglas Kim, Reston, VA (US); Karel Svoboda, Leesburg, VA (US); Loren Looger, Sterling, VA (US); Eric Schreiter, Ashburn, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 16/198,166

(22) Filed: Nov. 21, 2018

(65) Prior Publication Data

US 2019/0153067 A1    May 23, 2019

Related U.S. Application Data

(60) Provisional application No. 62/589,739, filed on Nov. 22, 2017.

(51) Int. Cl.
  *C07K 14/72*   (2006.01)
  *A61K 38/00*   (2006.01)
  *C12N 15/85*   (2006.01)
  *G01N 33/50*   (2006.01)

(52) U.S. Cl.
  CPC ............ *C07K 14/723* (2013.01); *A61K 38/00* (2013.01); *C07K 2319/60* (2013.01); *G01N 33/5041* (2013.01)

(58) Field of Classification Search
  None
  See application file for complete search history.

(56) References Cited

U.S. PATENT DOCUMENTS

| | | | |
|---|---|---|---|
| 8,629,256 B2 | 1/2014 | Looger et al. | |
| 9,518,980 B2 | 12/2016 | Looger et al. | |
| 9,664,697 B2 | 5/2017 | Ai et al. | |
| 2011/0154515 A1 | 6/2011 | Griesbeck et al. | |
| 2014/0101785 A1* | 4/2014 | Looger | G01N 33/5041 800/3 |
| 2015/0226755 A1* | 8/2015 | Ai | G01N 33/84 424/9.6 |
| 2015/0315258 A1* | 11/2015 | Looger | C07K 14/4728 435/348 |
| 2017/0292943 A1 | 10/2017 | Looger et al. | |

FOREIGN PATENT DOCUMENTS

| | | |
|---|---|---|
| WO | WO 2011/056975 | 5/2011 |
| WO | WO 2014/059154 | 4/2014 |
| WO | WO 2017/048808 | 3/2017 |

OTHER PUBLICATIONS

Ohkura et al., An Improved Genetically Encoded Red Fluorescent Ca2+ Indicator for Detecting Optically Evoked Action Potentials. PLOSONE Published: Jul. 10, 2012, vol. 7, Issue 7, 1-7 • https://doi.org/10.1371/journal.pone.0039933 (Year: 2012).*
Akerboom et al., Crystal Structures of the GCaMP Calcium Sensor Reveal the Mechanism of Fluorescence Signal Change and Aid Rational Design , J.Biol. Chem., 284(10);6455-64 2009 (Year: 2009).*
Cai et al. "A Cell-Based Functional Assay Using a Green Fluorescent Protein-Based Calcium Indicator dCys-GCaMP," Assay and Drug Development Technologies, vol. 12, No. 6, dated Aug. 1, 2014, pp. 342-351.
PCT International Search Report in International Application No. PCT/US2018/062244, dated Feb. 19, 2019, 14 pages.
Airan et al., "Temporally precise in vivo control of intracellular signalling," Nature, 58(7241):1025-1029, dated Apr. 23, 2009, 5 pages.
Dana et al., "Sensitive red protein calcium indicators for imaging neural activity," eLife, 5:e12727, dated Mar. 24, 2016, 24 pages.
Hsu et al. "Molecular dissection of G protein preference using Gsx chimeras reveals novel ligand signaling of GPCRs," Am J Physiol Endocrinol Metab., 293(4):E1021-E1029, dated Jul. 24, 2007, 9 pages.
Muto et al., "Real-Time Visualization of Neuronal Activity during Perception", Current Biology, 23(4):307-11, dated Feb. 18, 2013, 5 pages.
Tian et al., "Imaging neural activity in worms, flies and mice with improved GCaMP calcium indicators," Nat. Methods, 6(12):875-881, dated Dec. 2009, 22 pages.
Wardill et al., "A Neuron-Based Screening Platform for Optimizing Genetically-Encoded Calcium Indicators," PLoS One, doi:10.1371/journal.pone.0077728, dated Oct. 14, 2013, 14 pages.
Zhang et al., "Evaluation of FLIPR Calcium 3 Assay Kit—A New No-Wash Fluorescence Calcium Indicator Reagent," J Biomol Screen, 8(5):571-577, dated Jul. 1, 2003, 7 pages.

* cited by examiner

*Primary Examiner* — Aurora M Fontainhas
(74) *Attorney, Agent, or Firm* — Fish & Richardson P.C.

(57) ABSTRACT

Genetically encoded calcium indicator (GECI) polypeptides and the nucleic acid molecules encoding such polypeptides are provided. In addition, methods of using such nucleic acids and polypeptides in methods of screening for agonists or antagonists of G-protein coupled receptor (GPCR) or ion channels and methods of monitoring neural activity also are provided.

20 Claims, No Drawings
Specification includes a Sequence Listing.

```
                        SEQUENCE LISTING

<160> NUMBER OF SEQ ID NOS: 8

<210> SEQ ID NO 1
<211> LENGTH: 1350
<212> TYPE: DNA
<213> ORGANISM: Artificial Sequence
<220> FEATURE:
<223> OTHER INFORMATION: Synthetically generated nucleic acid encoding
      peptide biosensor

<400> SEQUENCE: 1
atgggttctc atcatcatca tcatcatggt atggctagca tgactggtgg acagcaaatg       60
ggtcgggatc tgtacgacga tgacgataag gatctcgcca ccatggtcga ctcatcacgt      120
cgtaagtgga ataagacagg tcacgcagtc agagtgatag gtcggctgag ctcactcgag      180
aacgtctata tcaaggccga caagcagaag aacggcatca aggcgaactt ccacatccgc      240
cacaacatcg aggacggcgg cgtgcagctc gcctaccact accagcagaa cacccccatc      300
ggcgacggcc ccgtgctgct gcccgacaac cactacctga gcgtgcagtc caaactttcg      360
aaagacccca cgagaagcg cgatcacatg gtcctgctgg agttcgtgac cgccgccggg      420
atcactctcg gcatggacga gctgtacaag ggcggtaccg gagggagcat ggtgagcaag      480
ggcgaggagc tgttcaccgg ggtggtgccc atcctggtcg agctggacgg cgacgtaaac      540
ggccacaagt tcagcgtgtc cggcgagggt gagggcgatg ccacctacgg caagctgacc      600
ctgaagttca tctgcaccac cggcaagctg cccgtgccct ggcccaccct cgtgaccacc      660
ctgacctacg gcgtgcagtg cttcagccgc taccccgacc acatgaagca gcacgacttc      720
ttcaagtccg ccatgcccga aggctacatc caggagcgca ccatcttctt caaggacgac      780
ggcaactaca agacccgcgc cgaggtgaag ttcgaggcg acaccctggt gaaccgcatc      840
gagcttaagg gcatcgactt caaggaggac ggcaacatcc tggggcacaa gctggagtac      900
aaccttcctg accaactgac tgaagagcag atcgcagaat ttaaagagct tttctcccta      960
tttgacaagg acggggatgg gacaataaca accaaggagc tggggacggt gatgcggtct     1020
```

```
ctggggcaga accccacaga agcagagctg caggacatga tcaatgaagt agatgccgac    1080
ggtgacggca caatcgactt ccctgagttc ctgacaatga tggcaagaaa aatgaaatac    1140
agggacacgg aagaagaaat tagagaagcg ttcggtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                    1350

<210> SEQ ID NO 2
<211> LENGTH: 450
<212> TYPE: PRT
<213> ORGANISM: Artificial Sequence
<220> FEATURE:
<223> OTHER INFORMATION: Synthetic peptide biosensor

<400> SEQUENCE: 2
```

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
                35                  40                  45

Ala Val Arg Val Ile Gly Arg Leu Ser Ser Leu Glu Asn Val Tyr Ile
50                  55                  60

Lys Ala Asp Lys Gln Lys Asn Gly Ile Lys Ala Asn Phe His Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
                115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
                195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
                275                 280                 285

Glu Asp Gly Asn Ile Leu Gly His Lys Leu Glu Tyr Asn Leu Pro Asp
290                 295                 300

```
Gln Leu Thr Glu Glu Gln Ile Ala Glu Phe Lys Glu Leu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Arg Asp Thr Glu
370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 3
<211> LENGTH: 1350
<212> TYPE: DNA
<213> ORGANISM: Artificial Sequence
<220> FEATURE:
<223> OTHER INFORMATION: Synthetically generated nucleic acid encoding
      peptide biosensor

<400> SEQUENCE: 3
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa caccccatc      300 ggcgacggcc ccgtgctgct gcccgacaac cactacctga gcgtgcagtc caaactttcg     360
aaagacccca cgagaagcg cgatcacatg gtcctgctgg agttcgtgac cgccgccggg      420
atcactctcg gcatggacga gctgtacaag gcggtaccg agggagcat ggtgagcaag       480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagcttaagg gcatcgactt caaggaggac ggcaacatcc tggggcacaa gctggagtac     900
aacctgccgg accaactgac tgaagagcag atcgcagaat ttaagagct gttctcccta     960 tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa aatgaaatac    1140
```

```
acagacagtg aagaagaaat tagagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                     1350
```

<210> SEQ ID NO 4
<211> LENGTH: 450
<212> TYPE: PRT
<213> ORGANISM: Artificial Sequence
<220> FEATURE:
<223> OTHER INFORMATION: Synthetic peptide biosensor

<400> SEQUENCE: 4

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Lys Trp Asn Lys Thr Gly His
                35                  40                  45

Ala Val Arg Ala Ile Gly Arg Leu Ser Ser Leu Glu Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
                115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
                195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
                275                 280                 285

Glu Asp Gly Asn Ile Leu Gly His Lys Leu Glu Tyr Asn Leu Pro Asp
                290                 295                 300

Gln Leu Thr Glu Glu Gln Ile Ala Glu Phe Lys Glu Leu Phe Ser Leu
305                 310                 315                 320
```

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 5
<211> LENGTH: 1350
<212> TYPE: DNA
<213> ORGANISM: Artificial Sequence
<220> FEATURE:
<223> OTHER INFORMATION: Synthetically generated nucleic acid encoding
      peptide biosensor

<400> SEQUENCE: 5
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca acgagaagcg cgatcacatg gtcctgctgg agttcgtgac cgccgccggg     420
atcactctcg gcatggacga gctgtacaag gcggtaccg  agggagcat ggtgagcaag     480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagcttaagg gcatcgactt caaggaggac ggcaacatcc tggggcacaa gctggagtac     900 aacccaccctg accaactgac tgaagagcag atcgcagaat taaagagct tttctcccta     960 tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca aatcgacttt ccctgagttc ctgacaatgt acgcaagaaa aatgaaatac    1140
agggacacga agaagaaat tagagaagcg ttcgtgtgt tgataagga tggcaatggc     1200 tacatcagtg cagcagagct tcgccacgtg atgacaaacc ttggagagaa gttaacagat    1260

```
gaagaggttg atgaaatgat cagggaagca gacatcgatg gggatggtca ggtaaactac   1320
gaagagtttg tacaaatgat gacagcgaag                                    1350
```

<210> SEQ ID NO 6
<211> LENGTH: 450
<212> TYPE: PRT
<213> ORGANISM: Artificial Sequence
<220> FEATURE:
<223> OTHER INFORMATION: Synthetic peptide biosensor

<400> SEQUENCE: 6

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Pro Pro Asp
290                 295                 300

Gln Leu Thr Glu Glu Gln Ile Ala Glu Phe Lys Glu Leu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
```

```
                340             345              350
Met Ile Asn Glu Val Asp Ala Asp Gly Asp Gly Thr Ile Asp Phe Pro
            355                 360                 365

Glu Phe Leu Thr Met Tyr Ala Arg Lys Met Lys Tyr Arg Asp Thr Glu
    370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
                435                 440                 445

Ala Lys
    450

<210> SEQ ID NO 7
<211> LENGTH: 1350
<212> TYPE: DNA
<213> ORGANISM: Artificial Sequence
<220> FEATURE:
<223> OTHER INFORMATION: Synthetically generated nucleic acid encoding
      peptide biosensor

<400> SEQUENCE: 7
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcacagcct     180
aacgtctata tcaaggccga caagcagaag acggcatca aggcgaactt caagatccgc      240
cacaacatcg aggacggcgg cgtgcagctc gcctaccact accagcagaa cacccccatc     300
ggcgacggcc ccgtgctgct gcccgacaac cactacctga gcgtgcagtc caaacttttcg    360 aaagacccca acgagaagcg cgatcacatg gtcctgctgg agttcgtgac cgccgccggg     420
atcactctcg gcatggacga gctgtacaag ggcggtaccg agggagcat ggtgagcaag      480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aaccttcctg accaactgac tgaagagcag atcgcagaat ttaaagagct tttctcccta     960
tttgacaagg acggggatgg acaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa agggagctac    1140
agggacagtg aagaagaaat tagagaagcg ttcggtgtgt ttgataagga tggcaatggc    1200
tacatcagtg cagcagagct tcgccacgtg atgacaaacc ttggagagaa gttaacagat    1260
gaagaggtta atgaaatgat cagggaagca gacatcgatg gggatggtca ggtaaactac    1320
gaagagtttg tacaaatgat gacagcgaag                                    1350
```

<210> SEQ ID NO 8
<211> LENGTH: 450
<212> TYPE: PRT
<213> ORGANISM: Artificial Sequence
<220> FEATURE:
<223> OTHER INFORMATION: Synthetic peptide biosensor

<400> SEQUENCE: 8

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Gln Pro Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
290                 295                 300

Gln Leu Thr Glu Glu Gln Ile Ala Glu Phe Lys Glu Leu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365
```

```
Glu Phe Leu Thr Met Met Ala Arg Lys Gly Ser Tyr Arg Asp Ser Glu
    370             375             380

Glu Glu Ile Arg Glu Ala Phe Gly Val Phe Asp Lys Asp Gly Asn Gly
385             390             395             400

Tyr Ile Ser Ala Ala Glu Leu Arg His Val Met Thr Asn Leu Gly Glu
            405             410             415

Lys Leu Thr Asp Glu Glu Val Asp Glu Met Ile Arg Glu Ala Asp Ile
        420             425             430

Asp Gly Asp Gly Gln Val Asn Tyr Glu Glu Phe Val Gln Met Met Thr
        435             440             445

Ala Lys
450
```

GENETICALLY ENCODED CALCIUM INDICATORS AND METHODS OF USE

CROSS REFERENCE TO RELATED APPLICATION

This application claims the benefit of U.S. Application No. 62/589,739 filed Nov. 22, 2017. The disclosure of the prior application is considered part of and is incorporated by reference in the disclosure of this application.

BACKGROUND

Calcium is a universal second messenger regulating essential cellular signaling events in a broad range of cells, tissues and organisms. In neurons, action potentials (APs) trigger large and rapid changes in cytoplasmic free calcium. Similarly, activation of synaptic glutamate receptors during synaptic transmission produces $Ca^{2+}$ in dendritic spines. Calcium imaging using synthetic calcium indicators has been used to measure neuronal spiking and synaptic input across populations of neurons in vitro and in vivo. However, synthetic indicators are difficult to target to specific cell types or sub-cellular locations, and the loading procedures are invasive and damaging to neural tissue, precluding repeated, chronic in vivo measurements.

SUMMARY

In one aspect, a nucleic acid molecule encoding a genetically encoded calcium indicator (GECI) polypeptide is provided, wherein the GECI polypeptide comprises an amino acid sequence having at least 95% sequence identity to a sequence shown in SEQ ID NO:2, SEQ ID NO:4, SEQ ID NO:6, or SEQ ID NO:8. In some embodiments, the GECI comprises an amino acid sequence having at least 99% sequence identity to a sequence shown in SEQ ID NO:2, SEQ ID NO:4, SEQ ID NO:6, or SEQ ID NO:8. In some embodiments, the GECI comprises an amino acid sequence shown in SEQ ID NO:2, SEQ ID NO:4, SEQ ID NO:6, or SEQ ID NO:8. In some embodiments, the nucleic acid has the sequence shown in SEQ ID NO:1, SEQ ID NO:3, SEQ ID NO:5, or SEQ ID NO:7. Also provided is a vector comprising any of the above-described nucleic acid molecules. Also provided is a cell comprising such a vector, or a cell comprising any of the above-described nucleic acid molecule.

In another aspect, a GECI polypeptide is provided, wherein the polypeptide comprises an amino acid sequence having at least 95% sequence identity to a sequence shown in SEQ ID NO:2, SEQ ID NO:4, SEQ ID NO:6, or SEQ ID NO:8. In some embodiments, the polypeptide comprises an amino acid sequence having at least 99% sequence identity to a sequence shown in SEQ ID NO:2, SEQ ID NO:4, SEQ ID NO:6, or SEQ ID NO:8. In some embodiments, the polypeptide comprises an amino acid sequence shown in SEQ ID NO:2, SEQ ID NO:4, SEQ ID NO:6, or SEQ ID NO:8. Also provided is a cell comprising any of the above-described polypeptides. In some embodiments, such a cell further comprises a nucleic acid molecule encoding a G-protein coupled receptor (GPCR) polypeptide. In some embodiments, such a cell further comprises a nucleic acid molecule encoding an ion channel. In some embodiments, the nucleic acid molecule encoding the GPCR polypeptide or the ion channel is heterologous to the cell.

In still another aspect, a method of screening agents for agonists or antagonists of G-protein coupled receptor (GPCR) polypeptides is provided. Generally, such a method includes (i) contacting a test agent with a cell comprising a GPCR polypeptide and a genetically encoded calcium indicator (GECI) polypeptide, wherein the GECI polypeptide comprises an amino acid sequence having at least 95% sequence identity to SEQ ID NO:2, SEQ ID NO:4, SEQ ID NO:6, or SEQ ID NO:8; and (ii) determining a level of fluorescence produced by the cell. Typically, an increase in fluorescence relative to a control indicates that the test agent is an agonist of the GPCR polypeptide, and a decrease in fluorescence relative to a control indicates that the test agent is an antagonist of the GPCR polypeptide. In some embodiments, the cell is in vitro. In some embodiments, the cell is in vivo (e.g., in a mouse, a worm, a rat, or a fly).

In some embodiments, the agent is selected from the group consisting of a nucleic acid, a polypeptide, a small molecule and combinations thereof. In some embodiments, the nucleic acid is an inhibitory nucleic acid. Representative inhibitory nucleic acids include, without limitation, a triplex forming oligonucleotide, an aptamer, a ribozyme, an antisense RNA, a short interfering RNA (siRNA), or a microRNA (miRNA). In some embodiments, the polypeptide is an antibody.

In still another aspect, a method of monitoring the activity of a cell is provided. Generally, such a method includes (i) providing a cell comprising a GPCR and a GECI, wherein the GECI comprises an amino acid sequence having at least 95% sequence identity to a sequence shown in SEQ ID NO:2, SEQ ID NO:4, SEQ ID NO:6, or SEQ ID NO:8; (ii) stimulating the cell; and (iii) detecting the fluorescence emitted by the cell. In some embodiments, the cell is provided in a biological sample from a subject (e.g., a mouse, a worm or a fly). In some embodiments, the detecting step comprises imaging. In some embodiments, the cell is a neuronal cell, a muscle cell or a cardiomyocyte.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Genetically encoded calcium indicators (GECIs) (also called fluorescent calcium indicator proteins; FCIPs) provide an alternative to synthetic indicators. GECIs can be easily targeted to specific cell types or sub-cellular compartments, and are compatible with long-term, repeated in vivo measurements. GECIs consist of a calcium-binding domain such as calmodulin or troponin C, fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs and multiple-FP GECIs, calcium binding modulates fluorescence resonance energy transfer (FRET) between FPs.

The calmodulin-based FRET indicator D3cpVenus (D3cpV) has recently been reported to detect single action potentials (APs) in pyramidal neurons in organotypic mouse brain slices and in vivo. The troponin C-based indicator TN-XXL has been used for chronic in vivo activity imaging in the mouse brain. Among single-FP based GECIs, the GCaMP family has found the broadest use across multiple model organisms. However, the properties of all available GECIs are still inferior to synthetic indicators in terms of signal-to-noise ratio (SNR), response linearity, photostability, and properly tuned calcium affinity. The GCaMP indicators further suffer from poor protein stability.

Nucleic Acid and Polypeptide Compositions

As described herein, improved GCaMP variants, referred to as "GCaMP7" variants (or "jGCaMP7" variants, to distinguish the sensors described herein from sensor described in Muto et al., 2013, Curr. Biol., 23(4):307-11 having a similar designation) were developed and characterized. As shown in the examples below, the jGCaMP variants described herein show dramatically improved responses in neurons to action potential (AP) stimulation, particularly for small numbers of APs. Thus, the variants disclosed herein are more sensitive at detecting neural activity than previous variants. Further, some of the variants disclosed herein show significantly faster rise and decay kinetics to AP-evoked calcium transients. Thus, some of the variants disclosed herein are better able to resolve and quantitate trains of APs and to precisely measure the times of APs. One of the variants disclosed herein also can be used to quantitate the difference between low and high numbers of APs. One of the variants disclosed herein is brighter in its calcium-unbound, resting state than previous variants. One of the variants disclosed herein also is dimmer in its calcium-unbound, resting state the previous variants while still exhibiting a high calcium-bound, activated fluorescence.

Provided herein are nucleic acid sequences encoding genetically encoded calcium indicators (GECIs) such as those designated jGCaMP7s, jGCaMP7f, jGCaMP7b, and jGCaMP7c. In some embodiments, the encoded jGCaMP7 polypeptide comprises the amino acid sequence shown in SEQ ID NO: 2, SEQ ID NO:4, SEQ ID NO:6, or SEQ ID NO:8, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO:4, SEQ ID NO:6, or SEQ ID NO:8 is expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present in SEQ ID NO: 2, SEQ ID NO:4, SEQ ID NO:6, or SEQ ID NO:8 can be substituted with a conservative amino acid(s), so long as the desired function of the peptide is maintained (e.g., substantially maintained). For example, in some instances, the nucleic acid sequence can comprise SEQ ID NO:1, SEQ ID NO:3, SEQ ID NO:5, or SEQ ID NO:7. In some embodiments, the nucleic acid sequence can consist or consist essentially of SEQ ID NO:1, SEQ ID NO:3, SEQ ID NO:5, or SEQ ID NO:7.

Also provided are jGCaMP7 polypeptides. For example, a jGCaMP7 polypeptide can have a sequence that comprises SEQ ID NO: 2, SEQ ID NO:4, SEQ ID NO:6, or SEQ ID NO:8, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO:4, SEQ ID NO:6, or SEQ ID NO:8 is expressed as a percentage of the total number of amino acids present. For example, about 0.5%, 1.0%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, or 30% (or a range between any of the aforementioned numbers) of the amino acids present in SEQ ID NO:2, SEQ ID NO:4, SEQ ID NO:6, or SEQ ID NO:8 can be substituted with a conservative amino acid(s), so long as the desired function of the peptide is maintained (e.g., substantially maintained)). In addition to a substitution, an insertion or a deletion can be introduced into a jGCaMP7 polypeptide. Insertions include the introduction of single or multiple amino acid residues, while deletions are characterized by the removal of one or more amino acid residues. Methods for predicting tolerance to protein modification are known in the art (see, e.g., Guo et al., 2004, PNAS USA, 101(25):9205-9210).

Nucleic acids that encode the polypeptide sequences, variants, and fragments thereof are disclosed. These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every nucleic acid sequence is in fact disclosed and described herein through the disclosed polypeptide sequences.

A GECI polypeptide provided herein, or a nucleic acid encoding such a GECI polypeptide, also provided herein, can have at least 70% sequence identity (e.g., at least 71%, 72%, 73%, or 74% sequence identity), at least 75% sequence identity (e.g., at least 76%, 77%, 78%, or 79% sequence identity), at least 80% sequence identity (e.g., at least 81%, 82%, 83%, or 84% sequence identity), at least 85% sequence identity (e.g., at least 86%, 87%, 88%, or 89% sequence identity), at least 90% sequence identity (e.g., at least 91%, 92%, 93%, or 94% sequence identity), at least 95% sequence identity (e.g., at least 96%, 97%, 98%, or 99% sequence identity) to a GECI polypeptide disclosed herein (e.g., SEQ ID NO:2, SEQ ID NO:4, SEQ ID NO:6, or SEQ ID NO:8) or a nucleic acid disclosed herein that encodes for a GECI polypeptide (e.g., SEQ ID NO:1, SEQ ID NO:3, SEQ ID NO:5, or SEQ ID NO:7).

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence disclosed herein (e.g., SEQ ID NOs:1-10) and another sequence, the default parameters of the respective programs are used.

TABLE 1

Conservative Amino Acid Substitutions

| Amino Acid | Representative Conservative Amino Acids |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

Modifications, including substitutions, insertions or deletions are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

As described above, the jGCaMP7 variants provided herein have the same or better characteristics than GCaMP3 (see, for example, WO 2011/056975 and Tian et al., 2009, Nat. Methods, 6(12):875-81) and the same or better characteristics than GCaMP5 and GCaMP6 variants (see, for example, WO 2014/059154). For example, the jGCaMP7 variants have one or more of the following characteristics: the same or better fluorescence change response to a single AP stimulus in neurons, the same or better calcium-induced, maximum fluorescence change, the same or lower calcium-unbound resting fluorescence, the same or better affinity for calcium than GCaMP3, the same or better protein stability as GCaMP3, the same or better photostability as GCaMP3, the same or higher cooperativity (Hill coefficient) as GCaMP3, the same or better brightness as GCaMP3, the same or better sensitivity as GCaMP3, and/or the same or better kinetics as GCaMP3. The jGCaMP7 variants described herein can be compared to GCaMP3, GCaMP5, and/or GCaMP6 using the methods described herein.

Also provided are vectors that include the GECI-encoding nucleic acid sequences disclosed herein. Typically, the GECI-encoding nucleic acid sequences comprise SEQ ID NO:1, SEQ ID NO:3, SEQ ID NO:5, or SEQ ID NO:7, and sequences with identity thereto, as noted above. Similarly, the GECI polypeptide typically comprises SEQ ID NO: 2, SEQ ID NO:4, SEQ ID NO:6, or SEQ ID NO:8, and sequences with identity thereto, as noted above. Examples of suitable vectors include, but are not limited to, plasmids, artificial chromosomes such as BACs, YACs, or PACs, and any of a number of viral vectors (e.g., retroviral vectors, replication-defective adenoviruses).

Vectors typically contain an origin of replication and one or more regulatory regions. Regulatory regions include, without limitation, promoters, enhancers, inducible elements, protein binding sequences, 5' or 3' untranslated regions (UTRs), transcriptional start sites, termination sequences, and polyadenylation sequences.

Promoters may be obtained from various sources including, for example, viruses such as polyoma, Simian Virus 40 (SV40), adenovirus, retroviruses, hepatitis B virus, and cytomegalovirus (CMV), or promoters from mammalian cells, e.g. beta-actin promoter or EF1-alpha promoter. In addition, promoters native to the host cell also are useful herein.

Enhancers refer generally to nucleic acid sequences that affect transcription of a sequence. Enhances typically are able to act at a distance from the transcribed sequence, be 5' or 3' to, or within an intron of, the transcribed sequence, and/or can be in cis orientation to the transcribed sequence. Many enhancer sequences are known from mammalian genes (globin, elastase, albumin, fetoprotein, and insulin), as well as from viruses (e.g., the SV40 enhancer on the late side of the replication origin, the cytomegalovirus early promoter enhancer, the polyoma enhancer on the late side of the replication origin, and adenovirus enhancers).

A promoter and/or an enhancer can be inducible (e.g. chemically or physically regulated). A chemically-induced promoter and/or enhancer can be regulated by the presence of, for example, alcohol, tetracycline, a steroid, or a metal. A physically-induced promoter and/or enhancer can be regulated by, for example, environmental factors such as temperature or light. On the other hand, a promoter and/or enhancer can be constitutive. In addition, certain promoters and/or enhancers can be active in a cell type-specific manner.

Vectors also can include a selectable marker. A selectable marker typically confers a phenotype on a cell and allows the cell to survive when placed under selective pressure. The product of the selectable marker can be used to confirm that the vector has been delivered to the cell and is being expressed. Examples of selectable markers include, without limitation, dihydrofolate reductase (DHFR), thymidine kinase, neomycin, neomycin analog G418, hygromycin, puromycin, blasticidin, beta-galactosidase, beta-glucuronidase, green fluorescent protein (GFP), and luciferase.

In addition, a vector can include a sequence encoding a tag, which is designed to facilitate manipulation or detection (e.g., purification or localization) of the expressed polypeptide. Sequences encoding tags such as GFP, glutathione S-transferase (GST), polyhistidine, c-myc, hemagglutinin, or FLAG™ tag (Kodak; New Haven, Conn.) typically are expressed as a fusion with the encoded polypeptide (e.g., at either the carboxyl or amino terminus or within the polypeptide).

Cells comprising the GECIs, the GECI-encoding nucleic acid sequences or vectors comprising the GECI-encoding nucleic acid sequence are provided. The cell can be, for example, a eukaryotic or prokaryotic cell. Suitable cells include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), and insect cells (for example, Sf9). Suitable cells also include, but are not limited to, human cells and plant cells. Representative human cells include, for example, HeLa cells or human embryonic kidney (HEK) cells. Cells that can be used herein are commercially available from, for example, the American Type Culture Collection (ATCC; PO Box 1549, Manassas, Va. 20108). See also Ausubel et al., 1998, Current Protocols in Molecular Biology, John Wiley & Sons, New York, N.Y. In some instances, the GECI-encoding nucleic acid sequence can be located in the genome of the cell. In some embodiments, the cell also includes a nucleic acid encoding a G-protein coupled receptor (GPCR) or an ion channel. Such a nucleic acid encoding a GPCR or an ion channel can be heterologous or endogenous to the cell.

Methods of introducing nucleic acids into cells are known and the method of transformation and choice of expression vector will depend on the host system selected. Transformation and transfection methods are described, e.g., in Ausubel et al. (1998, Current Protocols in Molecular Biology, John Wiley & Sons, New York, N.Y., (1998)), and, as described above, expression vectors may be chosen from examples known in the art. There are a number of compositions and methods which can be used to deliver the nucleic acid molecules and subsequently encoded polypeptides to cells, either in vitro or in vivo via. These methods and compositions can largely be broken down into two classes: viral-based delivery systems and non-viral-based delivery systems. Such delivery systems are well known in the art and are readily adaptable for use with the compositions and methods described herein.

Simply by way of example, polypeptides and/or nucleic acid molecules can be delivered via virus-like particles. Virus-like particles (VLPs) consist of viral protein(s) derived from the structural proteins of a virus. Methods for making and using virus-like particles are described in, for example, Garcea and Gissmann (2004, Current Opinion in Biotechnology, 15:513-7). Polypeptides also can be delivered by subviral dense bodies (DBs). DBs transport proteins into target cells by membrane fusion. Methods for making and using DBs are described in, for example, Pepperl-Klindworth et al. (2003, Gene Therapy, 10:278-84). In addition, polypeptides can be delivered by tegument aggregates. Methods for making and using tegument aggregates are described in WO 2006/110728.

Also provided are transgenic animals that include a GECI-encoding nucleic acid sequences described herein. "Animal" refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal in which one or more of the cells of the animal contain a heterologous nucleic acid. Methods for making transgenic animals have been described, for example, in Wagner et al. (1981, PNAS USA, 78:5016-5020); Stewart et al. (1982, Science, 217:1046-1048); Constantini et al. (1981, Nature, 294:92-94); Lacy et al. (1983, Cell, 34:343-358); McKnight et al. (1983, Cell, 34:335-341); Brinstar et al. (1983, Nature, 306:332-336); Palmiter et al. (1982, Nature, 300:611-615); Palmiter et al. (1982, Cell, 29:701-710); and Palmiter et al. (1983, Science, 222:809-814). Methods for making transgenic animals also are described in U.S. Pat. Nos. 6,175,057; 6,180,849; and 6,133,502.

One or more of the nucleic acid sequences, polypeptides, vectors or cells described herein, or combinations thereof, can be packaged into an article of manufacture (i.e., a kit) using containers, vials, or the like. For example, an article of manufacture can include (i) a nucleic acid sequence encoding a GECI, wherein the GECI has a sequence shown in SEQ ID NO: 2, SEQ ID NO:4, SEQ ID NO:6, or SEQ ID NO:8, or a variant of those sequences as discussed above; (ii) a GECI polypeptide having a sequence shown in SEQ ID NO: 2, SEQ ID NO:4, SEQ ID NO:6, or SEQ ID NO:8, or a variant of those sequences as discussed above; (iii) a vector comprising (i); (iv) a cell comprising (i); (v) a cell comprising (iii); or (vi) a cell comprising (ii). An article of manufacture as described herein can include any combination of (i)-(vi).

In addition, an article of manufacture as described herein can include one or more reagents, buffers, culture medium, neuronal or other type of cell, a G-protein coupled receptor (GPCR) polypeptide or a nucleic acid encoding a GPCR polypeptide, or an ion channel polypeptide or a nucleic acid encoding an ion channel polypeptide. An article of manufacture also can include instructions for use.

Methods of Using the Nucleic Acid and Polypeptide Compositions

The nucleic acid and polypeptide compositions described above, including, for example, vectors and cells containing such vectors, can be used in methods of screening for G-protein coupled receptor (GPCR) or ion channel agonists and antagonists. For example, a cell that expresses both a GPCR and one of the genetically encoded calcium indicators (GECI) described herein (e.g., a nucleic acid having the sequence shown in SEQ ID NO:1, SEQ ID NO:3, SEQ ID NO:5, or SEQ ID NO:7 encoding a polypeptide having the sequence shown in SEQ ID NO: 2, SEQ ID NO:4, SEQ ID NO:6, or SEQ ID NO:8, respectively) or a cell that expresses both an ion channel and one of the GECIs described herein can be contacted with an agent to be tested, and the level of fluorescence determined.

Generally, using the methods described herein, an increase in fluorescence indicates that the agent is a GPCR or ion channel agonist, while a decrease in fluorescence indicates that the agent is a GPCR or ion channel antagonist. As indicated herein, the GPCR or ion channel can be endogenous to the cell, or can be heterologous to the cell. If the GPCR or ion channel is heterologous to the cell, the nucleic acid encoding the GPCR or ion channel can be on the same or a different vector from the nucleic acid encoding the GECI or ion channel. Fluorescence is routinely determined in laboratories, and the level of fluorescence can be determined using any type of fluorometer.

Those skilled in the art understand that a determination of an increase or a decrease in fluorescence in the presence of an agent requires the use of an appropriate control. By way of example, one appropriate control can be measuring the level of fluorescence in a cell before and/or after a treatment (i.e., contact with an agent); another appropriate control can be measuring the level of fluorescence in the absence of a treatment (i.e., contact with an agent).

As used herein, an agent that can be screened in the methods described herein includes, for example, a polypeptide, an antibody (e.g., polyclonal or monoclonal; human or humanized) a small molecule, a nucleic acid molecule, a peptidomimetic, or any combination thereof. Nucleic acid molecules used in a method of screening as described herein can be, for example, an inhibitory nucleic acid molecule. Inhibitory nucleic acid molecules include, for example, a triplex forming oligonucleotide, an aptamer, a ribozyme, a short interfering RNA (siRNA), a micro-RNA (miRNA), or antisense nucleic acid. These types of inhibitory nucleic acid molecules are well known in the art and methods of designing them and making them also are well known in the art.

As is understood in the art, a G-protein coupled receptor (GPCR) refers to any member of a superfamily of receptors that mediates signal transduction by coupling with a G protein and is associated with a change in Ca2+ signaling and/or concentration. This class of GPCRs acts through the Gq type of G proteins, which activate a phospholipase C (PLC) pathway, resulting in the hydrolysis of phosphoinositides to generate two classes of different second messengers, diacylglycerol and inositol phosphates. Diacylglycerol activates certain protein kinase Cs (PKCs) and certain inositol phosphates stimulate the mobilization of calcium from intracellular stores.

Exemplary GPCRs include, but are not limited to alpha-1 adrenergic receptors (α1-AR), urotensin (UT) receptors, 5-HT2 and 5-HT6 serotonin receptors, hypocretin (orexin) receptors, histamine H1 receptors, bradykinin B1 and B2 receptors, bombesin BB2 receptors, P2Y purinergic receptors, acetylcholine receptors (e.g., M1, M3 and M5), mGluR5 glutamate receptors, vasopressin V2 and V1 receptors, angiotensin AGTR1 receptors, cholecystokinin CCKAR and CCKBR receptors, endothelin ENDRA receptors, ghrelin GHSR1a receptors, melatonin MTNR1A receptors, neurotensin NTSR1 receptors, platelet-activating factor PTAFR receptors, and prolactin releasing peptide receptor PRLHR receptors.

It is also possible to study Gs- and Gi-coupled receptors by co-expressing a cAMP-gated Ca2+ channel (Airan et al., 2009, Nature, 458(7241):1025-1029). This is carried out by taking advantage of the promiscuous G-protein G15/16 (Zhang et al., 2003, J Biomol Screen, 8(5):571-577), or by using chimeric G-proteins (Hsu and Luo, 2007, Am J Physiol Endocrinol Metab., 293(4):E1021-E1029). Such receptors include, but are not limited to, G-coupled 5-HT6 and 5-HT7 serotonin receptors, Gi-coupled GABA-B, histamine H3, and mGluR2/4 glutamate receptors.

As is understood in the art, an ion channel refers to any member of a superfamily of proteins that mediate cation or anion conductance into a cell, either through molecule binding (ligand-gated ion channels), membrane depolarization (voltage-gated ion channels), temperature stimulus (temperature-gated ion channels), force stimulus (force-gated ion channels), light stimulus (light-gated ion channels), pressure stimulus (pressure-gated ion channels), or other stimuli. Suitable ion channels for use with the GECIs described herein typically are calcium ion channels.

Exemplary ligand-gated calcium channels include, but are not limited to, AMPA (α-amino-3-hydroxy-5-methyl-4-isoxazolepropionic acid) receptors including iGluR1, iGluR2, iGluR3, iGluR4; NMDA (N-methyl-D-aspartate) receptors including NR1 and NR2; kainate receptors including iGluR5, iGluR6, iGluR7, KA1, and KA2; nicotinic acetylcholine receptors including alpha9, alpha10, alpha7, alpha8, alpha2, alpha3, alpha4, alpha6, beta2, beta4, beta3, alpha5, alpha1, beta1, gamma, delta, or epsilon nicotinic acetylcholine receptor subunits; P2X receptors; P2Y receptors; IP3 receptors; ryanodine receptors; two-pore calcium channels; and sperm cation channels. Representative voltage-gated calcium channels include, but are not limited to, L-type, N-type, P/Q-type, and R-type voltage-gated calcium channels such as CaV1.1, CaV1.2, CaV1.3, CaV1.4, CaV2.1, CaV2.2, CaV2.3, CaV3.1, CaV3.2, and CaV3.3. Exemplary temperature-gated calcium channels include, without limitation, transient receptor potential (TRP) channels including TRPC, TRPV, TRPA, TRPM, TRPP, TRPML, and TRPN channels. Representative light-gated calcium channels include channelrhodopsin-2 (ChR2) and mutants thereof. Some of these calcium ion channels, such as the TRP channels, respond to other stimuli such as force and/or pressure.

The nucleic acid and polypeptide compositions described above, including, for example, expression vectors and cells containing such expression vectors, can be used in methods of determining the calcium ion status of a cell. In addition, the nucleic acid and polypeptide compositions described above can be used in methods of monitoring neuronal activity. As discussed in more detail below, neuronal activity can be monitored in neuronal cells that are expressing a nucleic acid encoding a GECI polypeptide as described herein (e.g., a nucleic acid encoding a polypeptide having the sequence shown in SEQ ID NO: 2, SEQ ID NO:4, SEQ ID NO:6, or SEQ ID NO:8), and detecting the fluorescence emitted by the cells. Neuronal activity can be natural (e.g. neurons in the brain of an animal that is behaving, or a brain slice exhibiting spontaneous activity), or can be elicited by a chemical stimulus, an electrical stimulus, or another type of stimulus. A chemical stimulus can include a drug or combination of drugs, a toxin, a neurotransmitter, or any other compound. An electrical stimulus can be delivered, for example, from an extracellular electrode, or from an intracellular electrode, a magnetic resonance imaging (MRI) device, or any other type of electrical stimulus.

The neuronal cells can be contacted with the stimulus in vitro (e.g., in cell culture) or in vivo (e.g., in an animal such as, without limitation, a mouse, a worm, a rat, or a fly). Neuronal activity is used herein as an example, but those skilled in the art would understand that the activity of other cells types can be examined. For example, the activity of muscle cells, cardiomyocytes, or astrocytes and other glial cells can be evaluated using the compositions and methods described herein. Other cell types that can evaluated using the compositions and methods described herein include bacteria, single-cell pathogens, or cells in nematodes, insects, arachnids, and other animals.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Performance of jGCaMP7 Calcium Sensors

Table 1 shows a summary of performance of jCGaMP7 calcium sensors evaluated in dissociated rat cultured neurons. Action potentials were evoked by field stimulation, and fluorescence responses were imaged using the methods described in Wardill et al. (2013, PLoS One, doi:10.1371/journal.pone.0077728) and Dana et al. (2016, eLife, 5:e12727).

TABLE 1

Summary of Performance of jGCaMP7 Calcium Sensors

| Sensor | Resting fluorescence (normalized to GCaMP6s) | 1 AP peak ΔF/F0 (mean ± se) | 10 AP at 83 Hz peak ΔF/F0 | 160 AP at 83 Hz peak ΔF/F0 | Half decay time 10 Aps (ms) | Half rise time 10 Aps (ms) |
|---|---|---|---|---|---|---|
| GCaMP6s | 100.00% | 13.3 ± 0.5 | 213.6 ± 3.7 | 950 ± 10 | 1525 ± 11 | 115 ± 1 |
| GCaMP6f | 112.35% | 10.8 ± 0.7 | 169.2 ± 3.6 | 590 ± 8 | 335 ± 7 | 80 ± 1 |
| jGCaMP7s | 81.48% | 65.7 ± 4.8 | 373.3 ± 11.5 | 470 ± 26 | 1690 ± 55 | 70 ± 2 |
| jGCaMP7f | 87.65% | 31.6 ± 2.4 | 266.4 ± 9.5 | 525 ± 13 | 520 ± 15 | 75 ± 1 |
| jGCaMP7b | 169.27% | 40.6 ± 3.9 | 241.8 ± 8.3 | 385 ± 12 | 850 ± 25 | 80 ± 1 |
| jGCaMP7c | 59.26% | 22.3 ± 2.8 | 271.8 ± 13.2 | 1210 ± 77 | 900 ± 55 | 85 ± 3 |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A GECI polypeptide, wherein the polypeptide comprises an amino acid sequence having the sequence shown in SEQ ID NO: 2, SEQ ID NO:4, SEQ ID NO:6, or SEQ ID NO:8.

2. A cell comprising the polypeptide of claim 1.

3. A nucleic acid molecule encoding a genetically encoded calcium indicator (GECI) polypeptide, wherein the GECI polypeptide comprises the amino acid sequence shown in SEQ ID NO:2, SEQ ID NO:4, SEQ ID NO:6, or SEQ ID NO:8.

4. The nucleic acid molecule of claim 3, having the sequence shown in SEQ ID NO:1, SEQ ID NO:3, SEQ ID NO:5, or SEQ ID NO:7.

5. A vector comprising the nucleic acid molecule of claim 3.

6. A cell comprising the vector of claim 5.

7. A cell comprising the nucleic acid molecule of claim 3.

8. A method of screening agents for agonists or antagonists of G-protein coupled receptor (GPCR) polypeptides, comprising:
   (i) contacting a test agent with a cell comprising a GPCR polypeptide and a genetically encoded calcium indicator (GECI) polypeptide, wherein the GECI polypeptide comprises the amino acid sequence shown in SEQ ID NO: 2, SEQ ID NO:4, SEQ ID NO:6, or SEQ ID NO:8; and
   (ii) determining a level of fluorescence produced by the cell, wherein an increase in fluorescence relative to a control indicates that the test agent is an agonist of the GPCR polypeptide and wherein a decrease in fluorescence relative to a control indicates that the test agent is an antagonist of the GPCR polypeptide.

9. The method of claim 8, wherein the cell is in vitro.

10. The method of claim 8, wherein the cell is in vivo.

11. The method of claim 10, wherein the cell is in vivo in a mouse, a worm, a rat, or a fly.

12. The method of claim 8, wherein the agent is selected from the group consisting of a nucleic acid, a polypeptide, a small molecule and combinations thereof.

13. The method of claim 12, wherein the nucleic acid is an inhibitory nucleic acid.

14. The method of claim 13, wherein the inhibitory nucleic acid is a triplex forming oligonucleotide, an aptamer, a ribozyme, an antisense RNA, a short interfering RNA (siRNA), or a micro-RNA (miRNA).

15. The method of claim 12, wherein the polypeptide is an antibody.

16. A method of monitoring the activity of a cell, comprising:
   (i) providing a cell comprising a GPCR and a GECI, wherein the GECI comprises the amino acid sequence shown in SEQ ID NO: 2, SEQ ID NO:4, SEQ ID NO:6, or SEQ ID NO:8;
   (ii) stimulating the cell; and
   (iii) detecting the fluorescence emitted by the cell.

17. The method of claim 16, wherein the cell is provided in a biological sample from a subject.

18. The method of claim 17, wherein the subject is a mouse, a worm or a fly.

19. The method of claim 16, wherein the detecting step comprises imaging.

20. The method of claim 16, wherein the cell is a neuronal cell, a muscle cell or a cardiomyocyte.

* * * * *